(12) United States Patent
Ganesan et al.

(10) Patent No.: US 7,348,439 B2
(45) Date of Patent: Mar. 25, 2008

(54) 2-ARYL-3-(AMINOARYL)-3-(HYDROXYARYL)PHTHALIMIDINE COMPOUNDS AND METHODS FOR MAKING THEM

(75) Inventors: Balakrishnan Ganesan, Karnataka (IN); Gurram Kishan, Karnataka (IN); Pradeep Jeevaji Nadkarni, Karnataka (IN); Vinod Kumar Rai, Karnataka (IN); C. Seetharaman, Karnataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/289,250

(22) Filed: Nov. 29, 2005

(65) Prior Publication Data

US 2007/0123714 A1    May 31, 2007

(51) Int. Cl.
C07D 209/04    (2006.01)
(52) U.S. Cl. ..................... 548/469; 548/484
(58) Field of Classification Search .......... 548/469, 548/484
See application file for complete search history.

(56) References Cited

U.S. PATENT DOCUMENTS

| 5,344,910 A | 9/1994 | Sybert .................. 528/201 |
| 5,455,310 A | 10/1995 | Hoover et al. ........... 525/431 |
| 2003/0181768 A1 | 9/2003 | O' Young et al. .......... 568/728 |
| 2005/0075520 A1 | 4/2005 | O' Young et al. .......... 568/728 |

FOREIGN PATENT DOCUMENTS

| EP | 1 582 549 A1 | 10/2005 |
| EP | 0158549 A | 10/2005 |
| JP | 03-070790 | 3/1991 |
| JP | 06-003838 | 1/1994 |
| JP | 06-082624 | 3/1994 |
| JP | 11-044948 | 2/1999 |
| JP | 2005-206834 A | 4/2005 |

OTHER PUBLICATIONS

Korshak et al., 1975, CAS: 83: 193966.*

M.S. Lin et al., "Polymers With Improved Flammability Characteristics. I. Phenolphthalein-Related Homopolymers"; Journal of Polymer Science: Polymer Chemistry Edition, vol. 19, 2659-2670 (1981).
M.S. Lin et al., "Thermal Degradation Study of Phenolphthalein Polycarbonate", Journal of Polymer Science: Polymer Chemistry Edition, vol. 19, 2773-2797 (1981).
PCT Search Report issued by the International Searching Authority, dated Apr. 17, 2007 for International Application NO. PCT/US2006/045519 (International filing date: Nov. 28, 2006).
Database Caplus [Online] Chemical Abstracts Service, Columbus, Ohio. US; XP002427663 accession No. 1975:593966 abstract & Korshack et al.: "Thermal stability of cardic polybenzoxazoies" Vysokomolekulyarnye Soedineniya, Serya A, vol. 16. No. 12, 1974, pp.2671-2679, "see RN: 55130-35-3".
W.R. Ordorff; R.R. Murray: "A new class of phthaiens-mixed phthaleins-formed by heating p-hydroxybenzoyl-o-benzoic acids with phencis" J. Am. Chem. Soc, vol. 39, 1917, pp.679-697, XP002427655 p. 593.
Korshak V V et al.: "Cardo Polymers" Reviews in Macromolecular Chemistry, Marcel Dekker, Inc. New York, US. vol. C11, No. 1, 1974, pp. 45-142, Xp0090198.30.
Corrected PCT Search Report issued by the International Searching Authority, dated May 14, 2007 for International Application No. PCT/US2006/045519 (International filing date; Nov. 28, 2006).

* cited by examiner

*Primary Examiner*—Rei-tsang Shiao

(57) ABSTRACT

Compounds and methods for preparing 2-aryl-3-(aminoaryl)-3-(hydroxyaryl)phthalimidines having a formula of:

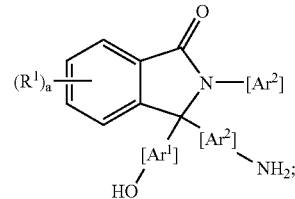

Figure 1:
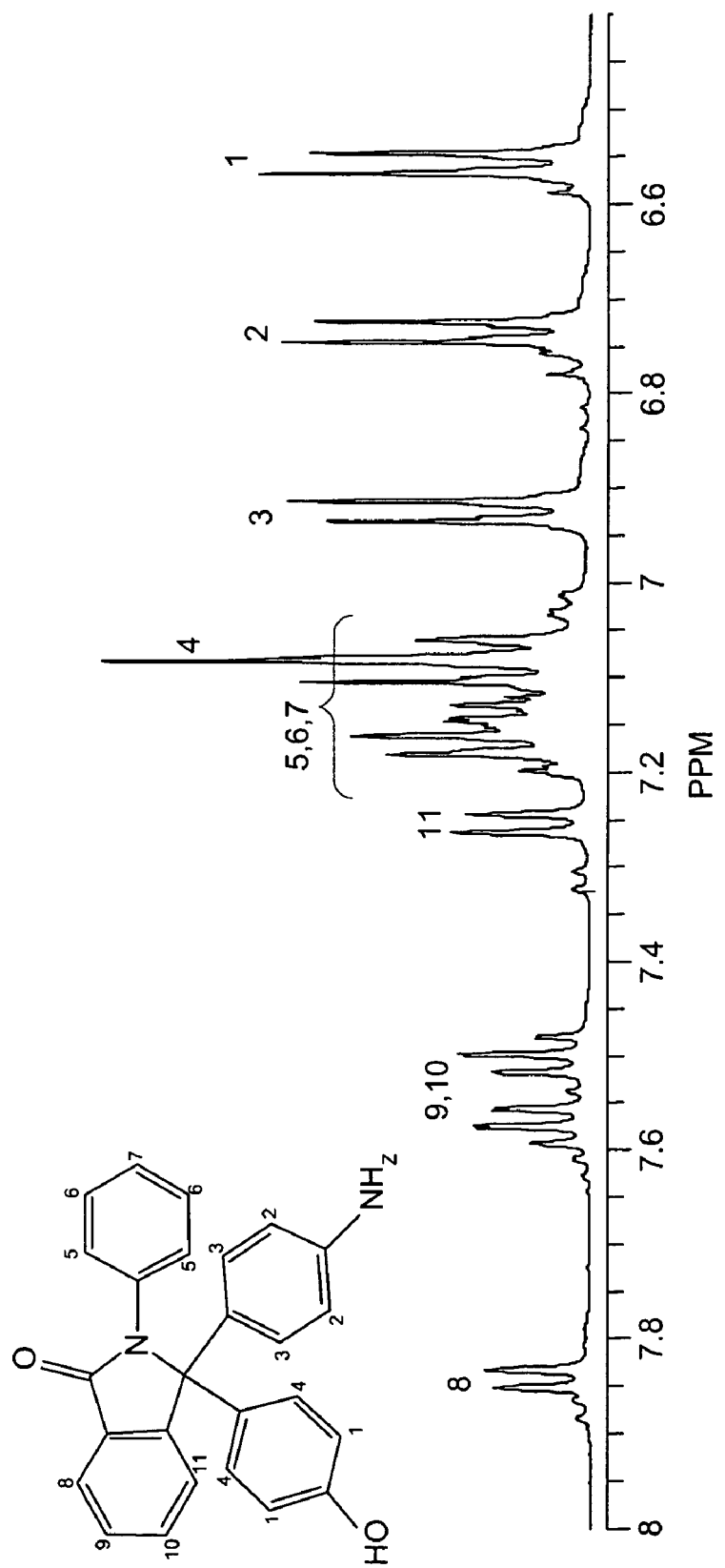

wherein $R^1$ is independently selected from a group consisting of a hydrocarbyl radical, a nitro radical, and a halogen atom; "a" is an integer from 0–4; and $Ar^1$ and $Ar^2$ are each independently an aromatic radical, are disclosed. The 2-aryl-3-(aminoaryl)-3-(hydroxyaryl)phthalimidine compounds are useful for preparing other useful monomers and polymers.

7 Claims, 1 Drawing Sheet

2-ARYL-3-(AMINOARYL)-3-(HYDROXYARYL)PHTHALIMIDINE COMPOUNDS AND METHODS FOR MAKING THEM

BACKGROUND

This disclosure relates generally to 2-aryl-3-(aminoaryl)-3-(hydroxyaryl)phthalimidine compounds and methods for preparing these compounds. Further, the disclosure relates to polymers including structural units derived from these compounds.

Polymers are important materials in modern commerce. A variety of polymers having commercial significance, such as polycarbonates, polyamides, polyurethanes, polyesters, and the like have been produced. Many of these polymers have been prepared from monomers that have two chemically identical reactive functional groups ("monofunctional monomers). Polymers prepared from bifunctional monomers, that is monomers having two chemically different reactive functional groups, are also known. Examples of such bifunctional monomers include aminophenols, aminocarboxylic acids, hydroxycarboxylic acids, compounds having an anhydride group and a hydroxy group, and the like. Bifunctional monomers can be useful for preparing polymers that have a combination of some of the desirable properties of the polymers prepared from monofunctional monomers that have only one or the other type of reactive functional groups of the bifunctional monomer.

There remains a need for bifunctional monomers that can be used for preparing polymers that potentially have a desirable combination of polymer physical properties, such as for example, high temperature stability, resistance to reaction with certain chemicals; high temperature stability and liquid crystalline behavior.

BRIEF SUMMARY

The present disclosure generally provides for novel 2-aryl-3-(aminoaryl)-3-(hydroxyaryl)phthalimidine compounds and methods for preparing them. These novel compounds are useful for preparing monomers and polymers comprising structural units derived from the 2-aryl-3-(aminoaryl)-3-(hydroxyaryl)phthalimidine compounds and functional monomers derived therefrom.

One embodiment is directed to a 2-aryl-3-(aminoaryl)-3-(hydroxyaryl)phthalimidine compound having a formula:

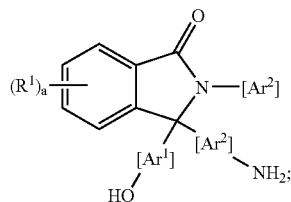

wherein $R^1$ is independently selected from a group consisting of a hydrocarbyl radical, a nitro radical, and a halogen atom; "a" is an integer from 0–4; and $Ar^1$ and $Ar^2$ are each independently an aromatic radical. To clarify, when "a" is less than 4, each unsubstituted carbon on the aryl ring is bonded to a hydrogen atom as is the accepted chemical shorthand. Further structures presented below are similar.

In another embodiment, a method for preparing a 2-aryl-3-(aminoaryl)-3-(hydroxyaryl)phthalimidine compound comprises reacting a precursor compound with a primary aromatic amine in the presence of an acidic catalyst, wherein the primary aromatic amine has a formula $Ar^1$—$NH_2$, wherein $Ar^1$ is an aromatic radical. The precursor compound is selected from the group consisting of a phenolphthalein compound, a 2-aryl-3,3-bis(hydroxyaryl)phthalimidine compound, and mixtures thereof.

In yet another embodiment, a method for preparing a 2-phenyl-3-(aminophenyl)-3-(hydroxyphenyl)phthalimidine compound comprises reacting a precursor compound with aniline in the presence of an acidic catalyst, wherein the precursor compound is selected from the group consisting of phenolphthalein, 2-phenyl-3,3-bis(4-hydroxyphenyl)phthalimidine, and mixtures thereof.

In still yet another embodiment, a polymer comprising structural units derived from at least one 2-aryl-3-(aminoaryl)-3-(hydroxyaryl)phthalimidine having a formula,

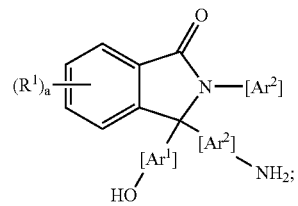

wherein $R^1$ is independently selected from a group consisting of a hydrocarbyl radical, a nitro radical, and a halogen atom; "a" is an integer from 0–4; and $Ar^1$ and $Ar^2$ are each independently an aromatic radical; is provided.

The disclosure may be understood more readily by reference to the following detailed description of the various features of the disclosure and the examples included therein.

FIGURE

The FIGURE shows the proton nuclear magnetic resonance spectrum of 2-phenyl-3-(4-aminophenyl)-3-(4-hydroxyphenyl)phthalimidine.

DETAILED DESCRIPTION

In the following description and claims that follow, reference will be made to a number of terms which shall be defined to have the following meanings: the singular forms "a", "an" and "the" include plural referents unless the context clearly dictates otherwise. "Optional" or "optionally" means that the subsequently described event or circumstance may or may not occur, and that the description includes instances where the event occurs and instances where it does not The term "hydrocarbyl radical" refers to an aliphatic radical, an aromatic radical, or a cycloaliphatic radical. The terms "formula" and "structure" are used interchangeably herein.

The term "aliphatic radical" refers to an organic radical having a valence of at least one comprising a linear or branched array of atoms which is not cyclic. The aliphatic radicals comprise at least one carbon atom. The array of atoms forming the aliphatic radical may further include heteroatoms such as nitrogen, sulfur, silicon, selenium and oxygen or may be composed exclusively of carbon and hydrogen. The "linear or branched array of atoms which is not cyclic" is intended to include a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, a suitable aliphatic radical is the 4-methylpent-1-yl radical, which is a $C_6$ aliphatic radical comprising a methyl group. Similarly, the 4-nitrobut-1-yl group is a $C_4$ aliphatic radical comprising a nitro functional group. Other suitable aliphatic radicals include a haloalkyl group that comprises one or more halogen atoms which may be the same or different. Suitable halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g.—$CH_2CHBrCH_2$—), and the like. Further examples of suitable aliphatic radicals include allyl, aminocarbonyl (—$CONH_2$), carbonyl, dicyanoisopropylidene (—$CH_2C(CN)_2CH_2$—), methyl (—$CH_3$), methylene (—$CH_2$—), ethyl, ethylene, formyl (—CHO), hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$), thiocarbonyl, trimethylsilyl (($CH_3)_3Si$—), t-butyldimethylsilyl, trimethoxysilylpropyl (($CH_3O)_3SiCH_2CH_2CH_2$—), vinyl, vinylidene, and the like. By way of further example, a $C_1$–$C_{10}$ aliphatic radical contains at least one but no more than 10 carbon atoms.

The term "aromatic radical" is also sometimes referred herein to as an "aryl radical". The aromatic radical or the aryl radical refers to an array of atoms having a valence of at least one comprising at least one aromatic group. The aromatic radical may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include non-aromatic components. For example, a benzyl group is an aromatic radical that comprises a phenyl ring (the aromatic group) and a methylene group (the non-aromatic component). Similarly a tetrahydronaphthyl radical is an aromatic radical comprising an aromatic group ($C_6H_3$) fused to a non-aromatic component —$(CH_2)_4$—. The "aromatic radical" can encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl alkyl group. Similarly, the 2-nitrophenyl group is a $C_6$ aromatic radical comprising a nitro functional group. Suitable aromatic radicals may include halogenated aromatic radicals such as trifluoromethylphenyl, hexafluoroisopropylidenebis(4-phen-1-yloxy) (—$OPhC(CF_3)_2PhO$—), chloromethylphenyl; 3-trifluorovinyl-2-thienyl; 3-trichloromethylphen-1-yl (3—$CCl_3Ph$—), 4(3-bromoprop-1-yl) phen-1-yl ($BrCH_2CH_2CH_2Ph$—), and the like. Further examples of aromatic radicals include 4-allyloxyphen-1-oxy, 4-aminophen-1-yl ($H_2NPh$—), 3-aminocarbonylphen-1-yl ($NH_2COPh$—), 4-benzoylphen-1-yl, dicyanoisopropylidenebis(4-phen-1-yloxy) (—$OPhC(CN)_2PhO$—), 3-methylphen-1-yl, methylenebis(phen-4-yloxy) (—$OPhCH_2PhO$—), 2-ethylphen-1-yl, phenylethenyl, 3-formyl-2-thienyl, 2-hexyl-5-furanyl; hexamethylene-1,6-bis(phen-4-yloxy) (—$OPh(CH_2)_6PhO$—); 4-hydroxymethylphen-1-yl (4-$HOCH_2Ph$—), 4-mercaptomethylphen-1-yl (4-$HSCH_2Ph$—), 4-methylthiophen-1-yl (4-$CH_3SPh$—), 3-methoxyphen-1-yl, 2-methoxycarbonylphen-1-yloxy (methyl salicyl), 2-nitromethylphen-1-yl, 3-trimethylsilylphen-1-yl, 4-t-butyldimethylsilylphenl-1-yl, 4-vinylphen-1-yl, vinylidenebis(phenyl), and the like. The term "a $C_3$–$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

The term "cycloaliphatic radical" refers to a radical having a valence of at least one and comprising an array of atoms that is cyclic but not aromatic. As defined herein a "cycloaliphatic radical" does not contain an aromatic group and may further include one or more noncyclic components. For example, a cyclohexylmethyl group ($C_6H_{11}CH_2$—) is a cycloaliphatic radical that comprises a cyclohexyl ring (the array of atoms is cyclic but not aromatic) and a methylene group (the noncyclic component). The cycloaliphatic radical may further include heteroatoms such as nitrogen, sulfur, selenium, silicon and oxygen, or may be composed exclusively of carbon and hydrogen. In addition, the cycloaliphatic radical can encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A suitable cycloaliphatic radical may also comprise one or more halogen atoms which may be the same or different. Suitable halogen atoms include, for example; fluorine, chlorine, bromine, and iodine. Suitable cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene2,2-bis (cyclohex-4-yl) (—$C_6H_{10}C(CF_3)_2 C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl ($H_2C_6H_{10}$—), 4-aminocarbonylcyclopent-1-yl ($NH_2COC_5H_8$—), 4-acetyloxycyclohex-1-yl, 2,2-dicyanoisopropylidenebis(cyclohex-4-yloxy)(—$OC_6H_{10}C(CN)_2C_6H_{10}O$—), 3-methylcyclohex-1-yl, methylenebis(cyclohex-4-yloxy) (—$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (—$O$ $C_6H_{10}(CH_2)_6$ $C_6H_{10}O$—); 4-hydroxymethylcyclohex-1-yl (4-$HOCH_2C_6H_{10}$—), 4-mercaptomethylcyclohex-1-yl (4-HSCH$_2$C$_6$H$_{10}$—), 4-methylthiocyclohex-1-yl (i.e. 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (NO$_2$CH$_2$C$_6$H$_{10}$O—), 3-trimethylsilylcyclohex-1-yl, 2-t-butyldimethylsilylcyclopent-1-yl, 4-trimethoxysilylethylcyclohex-1-yl ((CH$_3$O)$_3$SiCH$_2$CH$_2$C$_6$H$_{10}$—), 4-vinylcyclohexen-1-yl, vinylidenebis (cyclohexyl), and the like.

As disclosed herein, unless otherwise stated, the term "2-aryl-3,3-bis(hydroxyaryl)phthalimidine" (AHP) includes the ortho, para and para, para isomers, which generally refers to the placement of the OH functionality within the hydroxyaryl group. As disclosed herein, unless otherwise stated, the term "2-phenyl-3,3-bis(hydroxyphenyl)phthalimidine" (PPPBP) includes the ortho, para and the para, para isomers. As disclosed herein, the term "2-aryl-3-(aminoaryl)-3-(hydroxyaryl)phthalimidine" (AAHP) includes the para, para isomer, which refers to the placement of the OH and the NH$_2$ functional groups, unless otherwise indicated. As disclosed herein, the term "2-phenyl-3-(4-aminophenyl)-3-(4-hydroxyphenyl)phthalimidine" is interchangeable with the abbreviation "AP".

As disclosed herein, in the structures/formulae for the AAHPs, AHPs, or the phenolphthalein compounds, when the subscript "a" in "(R$^1$)a" is zero, it denotes a structure where all the R$^1$ substituents are hydrogen atoms. In the case where R$^1$ is other than a hydrogen atom, the subscript "a" can take values from zero to four, with a value of zero for "a" denoting a structure having only hydrogen atoms as the R$^1$ substituents.

The AAHP compounds have general formula (I),

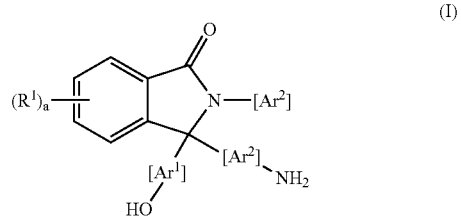
(I)

wherein R$^1$ is independently selected from a group consisting of a hydrocarbyl radical, a nitro radical, and a halogen atom; "a" is an integer from 0–4; and Ar$^1$ and Ar$^2$ are each independently an aromatic radical In an embodiment, AAHP compounds having formula (I) include those wherein Ar$^1$ and Ar$^2$ are each independently a monocyclic aromatic radical. In another embodiment, Ar$^1$ and Ar$^2$ are aryl radicals. In still another embodiment, Ar$^1$ and Ar$^2$ are each independently a monocyclic aromatic radical, and "a" is zero. In yet another embodiment, the 2-aryl-3-(aminoaryl)-3-(hydroxyaryl)phthalimidine has a formula (II),

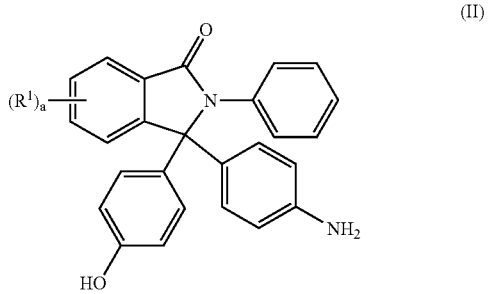
(II)

wherein R$^1$ is independently selected from a group consisting of a hydrocarbyl radical, a nitro radical, and a halogen atom; and "a" is an integer from 0–4. In still another embodiment, an exemplary 2-aryl-3-(aminoaryl)-3-(hydroxyaryl)phthalimidine has the structure (II), wherein R$^1$ is a hydrogen atom, and "a" is 4; also called 2-phenyl-3-(4-aminophenyl)-3-(4-hydroxyphenyl)phthalimidine (abbreviated herein as "AP").

The 2-aryl-3-(aminoaryl)-3-(hydroxyaryl)phthalimidines (AAHPs) are prepared by reacting a precursor compound with a primary aromatic amine having a general formula (III),

Ar$^2$—NH$_2$ (III)

wherein Ar$^2$ is an aromatic radical. Suitable primary aromatic amines include aniline and anilines substituted by one or more C$_1$–C$_{12}$ aliphatic radicals, one or more C$_3$–C$_{12}$ cycloaliphatic radicals, or one or more aromatic radicals.

The precursor compound can comprise a phenolphthalein compound having a formula (IV),

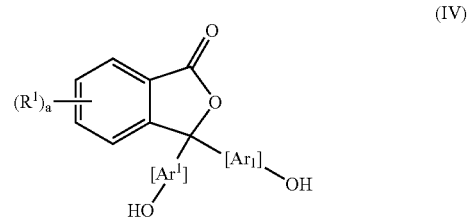
(IV)

wherein Ar$^1$, R$^1$, and "a" are as described previously for formula (I). Phenolphthalein compounds can be prepared by methods, such as for example, by the ring-alkylation reaction of a phthalic anhydride compound of formula (V),

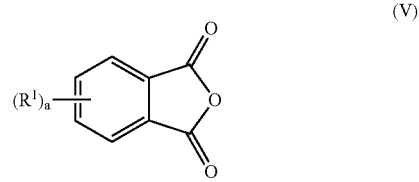
(V)

wherein R$^1$ and "a" are as described previously with an aromatic hydroxy compound of formula (VI),

Ar$^1$—OH (VI)

wherein Ar$^1$ is an aromatic radical.

A catalyst is generally employed for forming the phenolphthalein compounds. The catalyst may be a Lewis acid, such as for example, zinc chloride, aluminum chloride, ferric chloride, boron trifluoride, and the like. Non-limiting examples of phthalic anhydrides of formula (V) include phthalic anhydride, halogenated phthalic anhydrides, such as 3-chlorophthalic anhydride, 4-chlorophthalic anhydride, 3,4-dichlorophthalic anhydride, trichlorophthalic anhydride, tetrachlorophthalic anhydride, fluorophthalic anhydride, difluorophthalic anhydride, trifluorophthalic anhydride, tetrafluorophthalic anhydride, and the like; alkoxy-substituted phthalic anhydrides, nitrophthalic anhydrides, and the like. Phthalic anhydride is an exemplary phthalic anhydride compound since it is readily available commercially. The aromatic hydroxy compound of formula (VI) is exemplified by the parent compound, phenol, as well as any substituted phenol that can undergo the alkylation reaction with the phthalic anhydride compound. Some examples of substituted aromatic hydroxy compounds include the cresols (ortho, meta, para isomers), and xylenols (various isomers).

An exemplary phenolphthalein compound that can be used for preparing the AAHP compounds disclosed herein include the parent phenolphthalein having a formula (VII).

(VII)

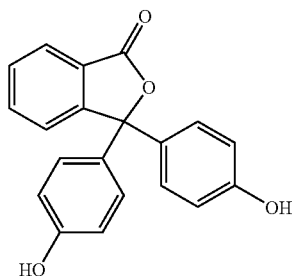

Suitable precursor compounds for preparing the AAHP compounds can also be a 2-aryl-3,3-bis(hydroxyaryl)phthalimidine of formula (VIII), (VIII)

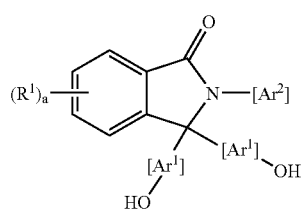

wherein $R^1$, "a", $Ar^1$ and $Ar^2$ are as previously described. In one embodiment, the 2-aryl-3,3-bis(hydroxyaryl)phthalimidine is of formula (IX), (IX)

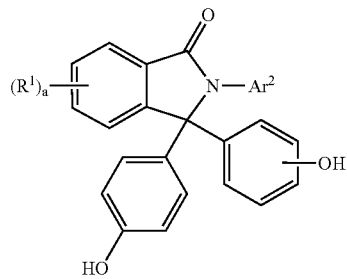

wherein $R^1$, "a", and $Ar^2$ are as previously described. In another embodiment, the 2-aryl-3,3-bis(hydroxyaryl)phthalimidine precursor includes varying amounts of the corresponding ortho, para-AHP, such as for example, the compound of general formula (X), (X)

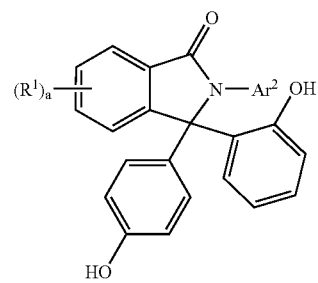

wherein $R^1$, "a", and $Ar^2$ are as previously described for formula (IX). 2-phenyl-3,3-bis(4-hydroxyphenyl)phthalimidine (para, para-PPPBP) is an exemplary 2-aryl-3,3-bis(hydroxyaryl)phthalimidine. The para, para-PPPBP may also comprise the corresponding ortho, para-isomer as the precursor compound.

The reaction of the aromatic primary amine with an AHP compound can be extended to other dihydroxy aromatic compounds that can undergo a similar reaction. This reaction can be regarded as a transarylation reaction in which a hydroxyphenyl group in the dihydroxy aromatic compound is exchanged for an aminoaryl group in the presence of an acidic catalyst. Non-limiting examples of dihydroxy aromatic compounds that can undergo such a transarylation reaction include compounds of formulas (XI)–(XIII).

(XI)

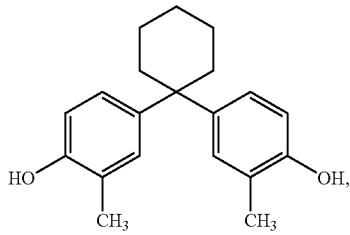

(XII)

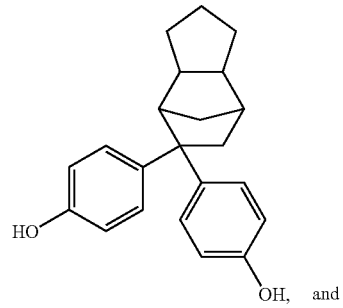

and (XIII)

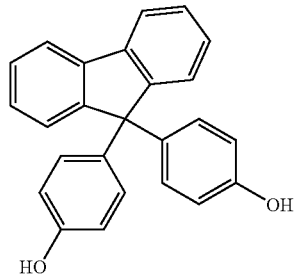

The products produced from the transarylation reaction include structures in which one or both hydroxyphenyl groups have been exchanged for the aminoaryl group, that is, —$NHAr^2$.

Suitable acidic catalysts used for forming the AAHP compounds comprise a salt of an organic amine and an acid. The acid is selected from the group consisting of an inorganic acid, an organic acid, or combinations of the foregoing acids. Some examples of inorganic acids include hydrochloric acid, sulfuric acid, phosphoric acid, and the like. Examples of organic acids include sulfonic acids, such as for example, methanesulfonic acid, ethanesulfonic acid, benzenesulfonic acid, dodecylbenzenesulfonic acid, and the like; and carboxylic acids, such as formic acid, benzoic acid, and the like. Polymeric acidic catalysts, such as those comprising sulfonic acid groups can also be used. Examples of polymeric acidic catalysts include cation exchange resins comprising sulfonic acid groups. Solid acidic catalysts, such as acidic silica, acidic alumina, and montmorillonite can also be used.

The organic amine needed to form the acidic catalyst can be a primary amine, a secondary amine, a tertiary amine, or any combination of the foregoing amines. Organic amines having one or more basic nitrogen atoms as part of a ring, such as for example, a pyridine compound can also be used. Further examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. In one embodiment, hydrochloride salts of the amines of formula (III) above, wherein $R^1$ is an aromatic radical, can be used. In another embodiment, acidic salts of primary aromatic amines that also serve as the starting material for preparing the AAHPs of formula (II) above are preferred. Aniline is an exemplary organic amine used for preparing an acidic catalyst to form the AAHP compounds.

In one embodiment, the acidic catalyst is introduced as a pre-formed salt into the reactor. In another embodiment, the catalyst is generated in situ within the reactor by first charging an amine of formula (III) into the reactor, and then adding an appropriate acid to the amine. For example, about 1/3 to about 1 part by weight of an acid, such as an inorganic acid can be added to the amine of formula (III) to generate the acidic salt catalyst. Hydrochloric acid is an exemplary inorganic acid. Hydrogen chloride gas can also be used. In one embodiment, about 0.1 parts to about 0.3 parts by weight of hydrogen chloride gas is introduced into a reactor charged with the organic amine, such as an aryl amine. The thus formed aryl amine hydrochloride can be suitably used as a catalyst in the present disclosure. Generally, a relatively higher level of the acidic catalyst favors the formation of the AAHP compounds. A solvent can optionally be employed to form the acidic catalyst, for example, the aryl amine hydrochloride. The solvent can then be removed (if necessary), and the hydrocarbyl amine of formula (III) can be added, followed by addition of the precursor compound of formula (IV) and/or (VIII).

When the precursor is the phenolphthalein compound, the reaction to form the desired products (I) proceeds with an intermediate formation of product having formula (VIII). The progress of the reaction can be followed by liquid chromatography, wherein the disappearance of the phenolphthalein compound and formation of the intermediate (VIII) and final product (I) can be monitored. The reaction temperature and reaction time can be adjusted to facilitate formation of product (I). The reaction of the phenolphthalein compound with the hydrocarbyl amine in the presence of the acidic catalyst proceeds by a condensation reaction to form the intermediate product having formula (VIII) and water by-product. The water can be removed by simply distilling it out of the reactor. Alternatively, the water can be removed as an azeotrope by using a suitable organic solvent. The intermediate product reacts with more hydrocarbyl amine in a second step in the presence of the acidic catalyst to form the desired product having formula (I). In the second step, an aromatic hydroxy compound is produced as a by-product. In an embodiment, the aromatic hydroxy compound can be removed during the reaction to facilitate the forward reaction. In another embodiment, the reaction mixture can be refluxed without removing the water or the aromatic hydroxy compound by-products. An excess of the aryl amine over the phenolphthalein may be used to keep the reaction proceeding in the forward direction. The temperature can be chosen so as to facilitate formation of the product. Generally, for a given pressure, a relatively higher temperature favors formation of the AAHP compound. The reaction can be conducted at a sub-ambient, ambient, or supra-ambient pressure. In an embodiment, a temperature of at least 100° C. can be used to form the AAHP compounds. The desired AAHP compounds can then be isolated from the reaction mixture by techniques known in the art for isolating organic amine compounds and/or aromatic hydroxy compounds.

The para, para-2-aryl-3,3-bis(hydroxyaryl)phthalimidines (AHP compounds), shown in formula (VIII) are produced as intermediates in the preparation of the AAHP compounds, and are themselves valuable as monomers for preparing polymers, such as polycarbonates. Hence, the reaction conditions to produce a AAHP compound can be modified or optimized to produce both a AHP compound and a AAHP compound as useful products.

The reaction mixture comprising the AAHP product also comprises the corresponding AHP by-product. Both products can exist as a mixture of para, para and ortho, para isomers. Generally, the para, para isomers of the AAH-P and AHP compounds predominate over the corresponding ortho, para isomers.

In one embodiment, the reaction mixture is first quenched with an aqueous mineral acid, such as aqueous hydrochloric acid. A solid mixture comprising the AAHP product and the AHP by-product results, which is filtered and dissolved in a mixture of water and an organic solvent, wherein the organic solvent can at least partly dissolve the solid mixture. The resulting solution is then contacted with an acidic material, which can bind the AAHP compound through the $NH_2$ group. Cation exchange resins having sulfonic acid groups can be used to separate the AAHP compound from the AHP compound. Any polar solvent that can at least partly dissolve the AAHP can be used. Further, these solvents may be at least partly miscible with water, or fully miscible with water. Suitable organic solvents comprise at least one functional group selected from the group consisting of a hydroxy group, a ketone carbonyl group, a carboxylic acid group, an ester group, a sulfoxide group, a nitrile group, an ether group, and a nitro group. In one embodiment, suitable organic solvents are those that comprise at least member selected from the group consisting of an organic hydroxy compound, an organic ketone, an organic amide, an organic sulfoxide, an organic ether, and an organic nitrile. Each of these categories of solvents may comprise more than one functional group, which may be the same or different from the other functional group(s). For example ethanol, ethylene glycol, and 2-ethoxyethanol may be used, either individually, or in any relative proportion as suitable organic solvents.

In one embodiment, aliphatic alcohols having at least one hydroxy group can be used as the organic solvent. Suitable organic hydroxy compounds include aliphatic, cycloaliphatic and aromatic hydroxy compounds having at least one hydroxy group. The aliphatic hydroxy compounds include linear and branched aliphatic mono-hydroxy compounds, non-limiting examples of which are methanol, ethanol, isopropanol, n-butanol, sec-butanol, iso-butanol, tert-butanol, and the like. Mixtures of these compounds can also be used. Aliphatic dihydroxy compounds, such as the glycols, exemplified by ethylene glycol, propylene glycol, and the like may also be used. Non-limiting examples of aromatic hydroxy compounds include phenol, ortho-cresol, benzyl alcohol, and the like. Some examples of cycloaliphatic hydroxy compounds include cyclopentanol, cyclohexanol, cyclohexanediol, and the like. In an embodiment, suitable organic hydroxy compounds include methanol, isopropanol, or any combination of methanol and isopropanol. Methanol is an exemplary organic solvent for that can be used isolating the AAHP compound, such as 2-phenyl-3-(4-aminophenyl)-3-(4-hydroxyphenyl)phthalimidine (AP).

Organic ketones suitable for use as the organic solvent include acetone, 2-butanone, methyl ethyl ketone, diethyl ketone, methyl isopropyl ketone, and the like. In an embodiment, the organic solvent comprises acetone. Suitable organic amides include formamide, acetamide, and the like. Organic sulfoxides that may be used as the organic solvent include dimethylsulfoxide, methyl ethyl sulfoxide, diethyl sulfoxide, and the like. Non-limiting examples of organic nitrites include the aliphatic nitriles, such as acetonitrile, propionitrile, butyronitrile, hexanedinitrile, and the like. Examples of organic nitro compounds that may be used include nitromethane, nitroethane, and the like.

In an embodiment, the organic solvent is methanol, ethanol, isopropanol, sec-butanol, phenol, acetone, butanone, formamide, or dimethylsulfoxide.

The cation exchange resin having the bound AAHP compound is then treated with a mixture comprising an aqueous acid and an organic solvent that can at least partly dissolve the AAHP compound. Examples of aqueous acids include aqueous mineral acids, such as hydrochloric acid, phosphoric acid, and the like. Examples of the organic solvent include those disclosed above. Aliphatic alcohols, such as methanol, ethanol, isopropanol, and the like are useful organic solvents. The acidic mixture liberates the free AAHP compound. The para, para isomer of AAHP can then be isolated in a pure form using a technique such as crystallization.

The AAHP compounds disclosed herein are valuable for making a variety of functional materials by selectively reacting either the NH$_2$ group, or the OH group with suitable reactants. Selective reaction of the NH$_2$ group gives rise to functional materials having a free OH group; and selective reaction of the OH group gives rise to functional materials having a free NH$_2$ group. For example, reaction of AP, shown below in formula (XIV):

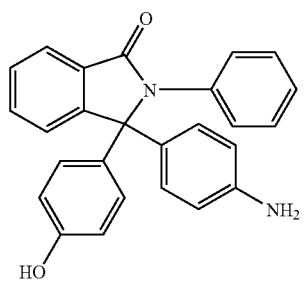

(XIV)

with an anhydride, such as phthalic anhydride provides the functional material of formula (XV):

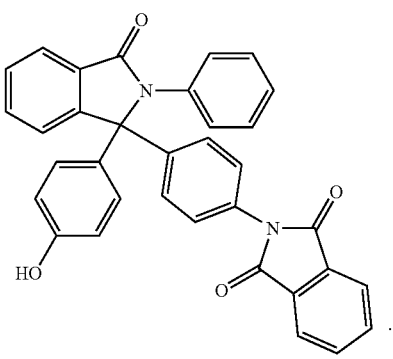

(XV)

The functional materials in turn can be used for preparing many different types of polymers.

The AAHP compounds are also valuable for making a variety of polymers. The polymers can be homopolymers, random copolymers, and block copolymers. The presence of the NH$_2$ and the aromatic hydroxy (OH) functional groups makes them suitable as monomers or comonomers for producing a variety of polymers comprising one or more types of structural units derived from these functional groups. Examples of such structural units include formulas (XVI)–(XX).

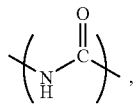

(XVI)

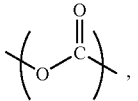

(XVII)

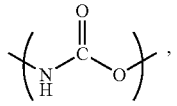

(XVIII)

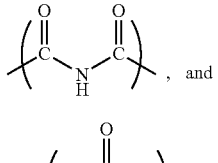

, and (XIX)

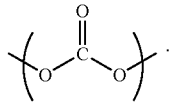

(XX)

Some non-limiting examples of polymers that can be produced using the AAHP compounds disclosed herein include, but are not limited to, polyesteramides, polyesterurethanes, polycarbonateamides, and the like.

The disclosure is explained in more detail with reference to the following non-limiting Examples, which are intended to be illustrative, not limitative.

EXAMPLES

Example 1

This example describes the procedure used for preparing the 2-phenyl-3-(4-hydroxyphenyl)-3-(4-aminophenyl)phthalimidine monomer from phenolphthalein and aniline as starting materials, and aniline hydrochloride as the catalyst.

A 500 milliliter 4-necked round-bottomed flask fitted with an overhead stirrer, a Dean-Stark apparatus, and a thermometer pocket was charged with aniline (83 grams, 0.88 mole), phenolphthalein (40.5 grams, 0.127 mole), and aniline hydrochloride (33 grams, 0.25 mole). The resulting mixture was heated to reflux with stirring (the temperature of the reacting mass was 180–185° C.) for 48 hours under a nitrogen atmosphere. Then, the reaction mass was cooled to 120–125° C., and treated with 5 weight percent aqueous hydrochloric acid. The resulting mixture was stirred for an additional 2 to 3 hours while maintaining the internal temperature at about 50° C., then cooled to ambient temperature, and filtered. The filter cake was washed thoroughly with water (5×100 milliliters) until the water wash was neutral (pH of about 7). Excess water from the filter cake was removed under suction, and the solid was dried at 100–120° C. to constant weight. The crude product thus obtained was analyzed by high pressure liquid chromatography (HPLC) and found to contain about 16 weight percent of AP.

About 100 grams of the crude product was dissolved in aqueous sodium hydroxide, stirred with 5 grams of activated carbon for about 15 minutes, and filtered. The filtrate was added to aqueous hydrochloric acid (containing 7–10 weight percent of dissolved HCl) with stirring to adjust the pH of the mixture to 3.5–4. After being stirred for another 30 minutes, and ensuring that the pH remained at about 3.5–4, the mixture was filtered and the filter cake was dried to constant weight. The material thus obtained was dissolved in 6 volumes (on a dry basis relative to the volume of the solid material) of a solvent containing 80:20 (volume/volume) of acetone and water, respectively. This solution was heated to a temperature of 40–45° C. and pumped through a column packed with 10 grams (on a dry basis) of a 2 percent crosslinked sulfonated polystyrene-divinylbenzene ion exchange resin at a weighted hourly space velocity of 6–7 (that is about 60–70 grams of the feed solution per hour). The level of AP in the effluent is monitored using HPLC. Generally, the feed solution was pumped through the column till the effluent had approximately 75 parts per million of AP. The pumping was stopped, and the liquid remaining in the column was drained out. Next, a solvent mixture containing 90:10:10 (volume by volume) of acetone, concentrated hydrochloric acid and water, respectively, was prepared and pumped through the column. Then, a solvent mixture containing 80:20 (volume by volume) of acetone and water, respectively was pumped through the column until the effluent had a neutral pH. The combined effluents was neutralized with an aqueous base containing a basic material, such as sodium hydroxide, sodium carbonate, or sodium bicarbonate. The entire mixture was evaporated to remove the solvents. The solid residue remaining was analyzed by HPLC to contain approximately 50 weight percent of AP. A portion of this material was subjected to preparatory HPLC using a mobile phase consisting of a 86:9:5 volume ratio of solvents (A), (B), and (C); wherein solvent (A) is a 0.02 weight percent solution of phosphoric acid in water, solvent (B) is methanol, and solvent (C) is acetonitrile. A column oven temperature of about 40° C., a flow rate of 1 milliliter per minute, and a detector wavelength of 270 nanometers was used for the preparative HPLC. The eluate containing the desired AP was collected and evaporated to furnish a pure sample of AP. The chemical identity of AP was established by proton nuclear magnetic resonance (NMR) spectroscopy. Referring to the FIGURE, the proton NMR spectrum shows the peaks with assignments to the various types of protons present in AP. The assignments are shown as numbers (1 through 10) in the FIGURE. Two-dimensional carbon-proton correlation spectroscopy was used to establish that the NH$_2$ and the phenolic OH groups were located at the para position of each phenyl ring in AP, thus confirming that the isolated material was the para, para-AP isomer.

Example 2

This example describes the procedure used for preparing the monomer 2-phenyl-3-(4-hydroxyphenyl)-3-(4-aminophenyl)phthalimidine (AP) from 2-phenyl-3,3-bis(4-hydroxyphenyl)phthalimidine and aniline as starting materials, and aniline hydrochloride as the catalyst.

The crude reaction product was obtained as described above in Example 1 by using aniline (83 grams; 0.88 mole), para, para-PPPBP (50 grams, 0.127 mole), and aniline hydrochloride (33 grams; 0.25 mole). The crude product contained about 16 weight percent of AP, as determined by HPLC. The isolation of pure para, para-AP was achieved by using the same procedure as described for Example 1.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A para, para-2-aryl-3-(aminoaryl)-3-(hydroxyaryl)phthalimidine having a formula:

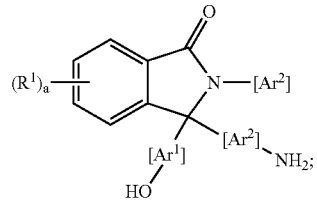

wherein $R^1$ is independently selected from a group consisting of a hydrocarbyl radical, a nitro radical, and a halogen atom; "a" is an integer from 0–4; and $Ar^1$ and $Ar^2$ are each independently an aromatic radical.

2. The para, para-2-aryl-3-(aminoaryl)-3-(hydroxyaryl) phthalimidine of claim 1, wherein $Ar^1$ and $Ar^2$ are each independently a monocyclic aromatic radical.

3. The para, para-2-aryl-3-(aminoaryl)-3-(hydroxyaryl) phthalimidine of claim 2, wherein $Ar^1$ and $Ar^2$ are phenylene radicals.

4. The para, para-2-aryl-3-(aminoaryl)-3-(hydroxyaryl) phthalimidine of claim 2, wherein "a" is 0.

5. The para, para-2-aryl-3-(aminoaryl)-3-(hydroxyaryl) phthalimidine of claim 1, having a formula:

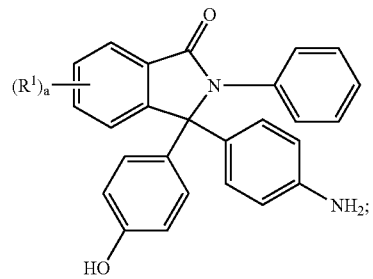

wherein $R^1$ is independently selected from a group consisting of a hydrocarbyl radical, a nitro radical, and a halogen atom; "a" is an integer from 0–4.

6. The para, para-2-aryl-3-aminoaryl)-3-(hydroxyaryl)phthalimidine of claim 5, wherein "a" is 0.

7. A 2-aryl-3-(aminoaryl)-3-(hydroxyaryl)phthalimidine having a formula:

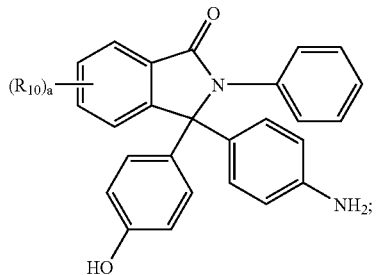

wherein $R^1$ is independently selected from a group consisting of a hydrocarbyl radical, a nitro radical, and a halogen atom; "a" is an integer from 0–4.

* * * * *